United States Patent
Ali et al.

(10) Patent No.: US 11,390,572 B2
(45) Date of Patent: Jul. 19, 2022

(54) PROCESS FOR PRODUCING LIGHT OLEFINS (ETHYLENE + PROPYLENE) AND BTX USING A MIXED PARAFFINIC $C_4$ FEED

(71) Applicant: SABIC Global Technologies B.V., Bergen op Zoom (NL)

(72) Inventors: Talal Ali, Riyadh (SA); Nabil Alyasser, Riyadh (SA); Ahmed S. Alzenaidi, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 17/250,530

(22) PCT Filed: Sep. 19, 2019

(86) PCT No.: PCT/IB2019/057920
§ 371 (c)(1),
(2) Date: Feb. 1, 2021

(87) PCT Pub. No.: WO2020/058904
PCT Pub. Date: Mar. 26, 2020

(65) Prior Publication Data
US 2021/0309591 A1 Oct. 7, 2021

Related U.S. Application Data

(60) Provisional application No. 62/733,766, filed on Sep. 20, 2018.

(51) Int. Cl.
*C07C 4/06* (2006.01)
*B01J 29/46* (2006.01)
(Continued)

(52) U.S. Cl.
CPC ............ *C07C 4/06* (2013.01); *B01J 29/46* (2013.01); *C07C 2/76* (2013.01); *C07C 4/04* (2013.01)

(58) Field of Classification Search
CPC ........... C10G 2400/20; C10G 2400/30; C10G 69/06; C10G 11/00; C10G 2300/1092;
(Continued)

(56) References Cited

U.S. PATENT DOCUMENTS

| 2007/0090020 A1 | 4/2007 | Buchanan et al. |
| 2010/0036182 A1 | 2/2010 | Forestiere et al. |

(Continued)

FOREIGN PATENT DOCUMENTS

CN 107879873 A * 9/2016

OTHER PUBLICATIONS

International Search Report and Written Opinion issued in Corresponding PCT Application No. PCT/IB2019/057920, dated Dec. 19, 2019.
(Continued)

*Primary Examiner* — Sharon Pregler
(74) *Attorney, Agent, or Firm* — Norton Rose Fulbright US LLP

(57) ABSTRACT

Systems and methods for producing light olefins and BTX are disclosed. A feed stream comprising mixed $C_4$ paraffins is first separated into a first stream comprising primarily isobutane, and a second stream comprising primarily n-butane. The first stream is processed in a catalytic cracking unit and the second stream is processed in a steam cracking unit. The resulting streams from the catalytic cracking unit and the steam cracking unit are separated to form product streams including an ethylene stream, a propylene stream, and a BTX stream.

20 Claims, 2 Drawing Sheets

(51) Int. Cl.
*C07C 2/76* (2006.01)
*C07C 4/04* (2006.01)

(58) Field of Classification Search
CPC .......... C10G 35/00; C10G 45/00; C07C 4/04;
C07C 7/04; C07C 11/04; C07C 11/06;
C07C 2/864; C07C 407/00; C07C 5/333;
C07C 11/09; C07C 15/08; C07C 409/04;
C07C 9/10; C07C 9/12; C07C 11/10;
C07C 4/06; C07C 5/05; C07C 5/11
See application file for complete search history.

(56) References Cited

U.S. PATENT DOCUMENTS

| | | |
|---|---|---|
| 2011/0040133 A1 | 2/2011 | Vermeiren et al. |
| 2013/0296622 A1 | 11/2013 | Iaccino et al. |
| 2014/0275673 A1 | 9/2014 | Long et al. |
| 2014/0357914 A1 | 12/2014 | Funk et al. |
| 2016/0369190 A1 | 12/2016 | Ward et al. |
| 2017/0009151 A1 | 1/2017 | Dittrich et al. |
| 2018/0057758 A1 | 3/2018 | Al-Ghamdi et al. |

OTHER PUBLICATIONS

Lu et al., "FeHZSM-5 molecular sieves—Highly active catalysts for catalytic cracking of isobutane to produce ethylene and propylene" *Catalysis Communications* 2006, 7(4), 199-203.

\* cited by examiner

PROCESS FOR PRODUCING LIGHT OLEFINS (ETHYLENE + PROPYLENE) AND BTX USING A MIXED PARAFFINIC $C_4$ FEED

CROSS REFERENCE TO RELATED APPLICATIONS

This application is a national phase application under 35 U.S.C. § 371 of International Application No. PCT/IB2019/057920 filed Sep. 19, 2019, which claims priority to and the benefit of U.S. Provisional Application No. 62/733,766, filed Sep. 20, 2018 all of which are incorporated into the present application by reference.

FIELD OF INVENTION

The present invention generally relates to a process of producing olefins and aromatics. More specifically, the present invention relates to an integrated process that includes splitting a mixture of isobutane and n-butane, steam cracking n-butane, and catalytically cracking isobutane in a catalytic cracking unit to produce light olefins, benzene, toluene, and xylene.

BACKGROUND OF THE INVENTION

Light olefins ($C_2$ to $C_4$ olefins) are building blocks for many chemical processes. Light olefins are used to produce polyethylene, polypropylene, ethylene oxide, ethylene chloride, propylene oxide, and acrylic acid, which, in turn, are used in a wide variety of industries such as the plastic processing, construction, textile, and automotive industries. Generally, light olefins are produced by steam cracking naphtha and dehydrogenation of paraffin.

BTX (benzene, toluene, and xylene) are a group aromatics that are used in many different areas of the chemical industry, especially the plastic and polymer sectors. For instance, benzene is a precursor for producing polystyrene, phenolic resins, polycarbonate, and nylon. Toluene is used for producing polyurethane and as a gasoline component. Xylene is feedstock for producing polyester fibers and phthalic anhydride. In the petrochemical industry, benzene, toluene, and xylene are conventionally produced by catalytic reforming of naphtha.

Over the last few decades, the demand for both light olefins and BTX has been consistently increasing. One of the conventional methods of producing light olefins and BTX includes steam cracking mixed $C_4$ paraffins. However, the overall efficiency for this conventional method is relatively low because isobutane, one of the major components of mixed $C_4$ hydrocarbons, has relatively low ethylene yield and generates a large amount of hydrocarbons recycled to the steam cracking unit. As hydrocarbons have to be hydrogenated before they are recycled back to the steam cracking unit, the large amount of hydrocarbons for recycling can demand a large amount of hydrogen and energy in the hydrogenation process, resulting in high production cost.

Overall, while methods of producing light olefins and BTX exist, the need for improvements in this field persists in light of at least the aforementioned drawbacks for the methods.

BRIEF SUMMARY OF THE INVENTION

A solution to at least some of the above-mentioned problems associated with the production process for light olefins and BTX using a mixture of $C_4$ paraffins has been discovered. The solution resides in a method of producing olefins that includes splitting the mixed $C_4$ paraffins into a first stream comprising primarily isobutane and a second stream comprising primarily n-butane, and processing the isobutane and the n-butane in a catalytic cracking unit and a steam cracking unit, respectively. This can be beneficial for at least improving the conversion rate of isobutane to light olefins and/or BTX and reducing the production cost for light olefins and BTX. Notably, this method uses catalytic cracking to process isobutane, which has a higher conversion rate to light olefins compared to conventional methods. Additionally, this method produces less hydrocarbons for recycling, resulting in reduced usage for hydrogen and energy in the hydrogenation of the $C_4$ olefins in the recycling stream. Therefore, the method of the present invention provides a technical solution for at least some of the problems associated with the currently available methods for producing light olefins mentioned above.

Embodiments of the invention include a method of producing olefins. The method comprises splitting a feed stream comprising primarily isobutane and n-butane, collectively, to form a first stream comprising primarily isobutane and a second stream comprising primarily n-butane. The method further comprises contacting the first stream with a catalyst under reaction conditions sufficient to cause cracking of at least some of the isobutane in the first stream to form one or more of: ethylene, propylene, benzene, toluene, and xylene. The method further still comprises subjecting the second stream to steam cracking at a temperature above 800° C. to form one or more of: ethylene, propylene, benzene, toluene, and xylene.

Embodiments of the invention include a method of producing olefins. The method comprises splitting a feed stream comprising primarily isobutane and n-butane, collectively, to form a first stream comprising primarily isobutane and a second stream comprising primarily n-butane. The method further comprises contacting the first stream with a catalyst comprising Fe modified HZSM-5 under reaction conditions sufficient to cause cracking of at least some of the isobutane in the first stream to form one or more of: ethylene, propylene, benzene, toluene, and xylene. The method further still comprises subjecting the second stream to a steam cracking process at a temperature above 800° C. to form one or more of: ethylene, propylene, benzene, toluene, and xylene.

Embodiments of the invention include a method of producing olefins. The method comprises splitting a feed stream comprising primarily isobutane and n-butane, collectively, to form a first stream comprising primarily isobutane and a second stream comprising primarily n-butane. The method further comprises contacting the first stream with a catalyst comprising Fe modified HZSM-5 under reaction conditions sufficient to cause cracking of at least some of the isobutane in the first stream to form one or more of: ethylene, propylene, benzene, toluene, and xylene, wherein the reaction conditions for the catalytic cracking comprise a temperature in a range of 575 to 625° C. The method further comprises subjecting the second stream to a steam cracking process at a temperature above 800° C. to form one or more of: ethylene, propylene, benzene, toluene, and xylene. The contacting step is carried out in a catalytic cracking zone and the subjecting step is carried out in a steam cracking zone. The method further comprises flowing an effluent from the catalytic cracking zone and an effluent from the steam cracking zone to a quenching and compression unit to form a combined quenched stream. The method further still comprises separating the combined quenched stream in a separation unit to produce a plurality of streams including an ethylene stream comprising primarily ethylene, a propylene stream comprising primarily propylene, a BTX stream comprising primarily BTX, a heavy stream comprising primarily fuel oil and heavy aromatics, and a recycle stream comprising 1-butene, 2-butene, butadiene, isobutylene, n-butane, isobutane, or combinations thereof. The method further still comprises hydrogenating at least some 1-butene, 2-butene, isobutylene, and/or butadiene of the recycle stream in a hydrogenation unit to produce a hydrogenated recycle stream, and flowing the hydrogenated recycle stream to the feed stream.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The term "raffinate," as the term is used in the specification and/or claims, means the rest of a product stream, from which a target component or components have been removed.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

Currently, light olefins and BTX can be produced by steam cracking mixed $C_4$ paraffins. However, the overall conversion rate to light olefins for this conventional method is relatively low because isobutane, which normally makes up about 70 wt. % of the mixed $C_4$ paraffins, has a low conversion rate to ethylene. Furthermore, the production costs for using the conventional method is high as steam cracking isobutane produces a large amount of raffinate, which needs to be hydrogenated before it is recycled back to the steam cracking unit. Thus, the large amount raffinate results in large demand for hydrogen and energy in the hydrogenation process. The present invention provides a solution to at least some of these problems. The solution is premised on a method including splitting the mixed $C_4$ paraffins into a first stream comprising primarily isobutane and a second stream comprising primarily n-butane. The isobutane is catalytically cracked and the n-butane is steam cracked. This method is capable of reducing the amount of raffinate produced by cracking isobutane, thereby reducing the energy cost and hydrogen cost for hydrogenating the raffinate. Additionally, this method is capable of increasing the conversion rate of isobutane and the productivity of light olefins, resulting in improved production efficiency. These and other non-limiting aspects of the present invention are discussed in further detail in the following sections.

A. System for Processing Mixed $C_4$ Paraffins and Producing Olefins and BTX

Figure 1:
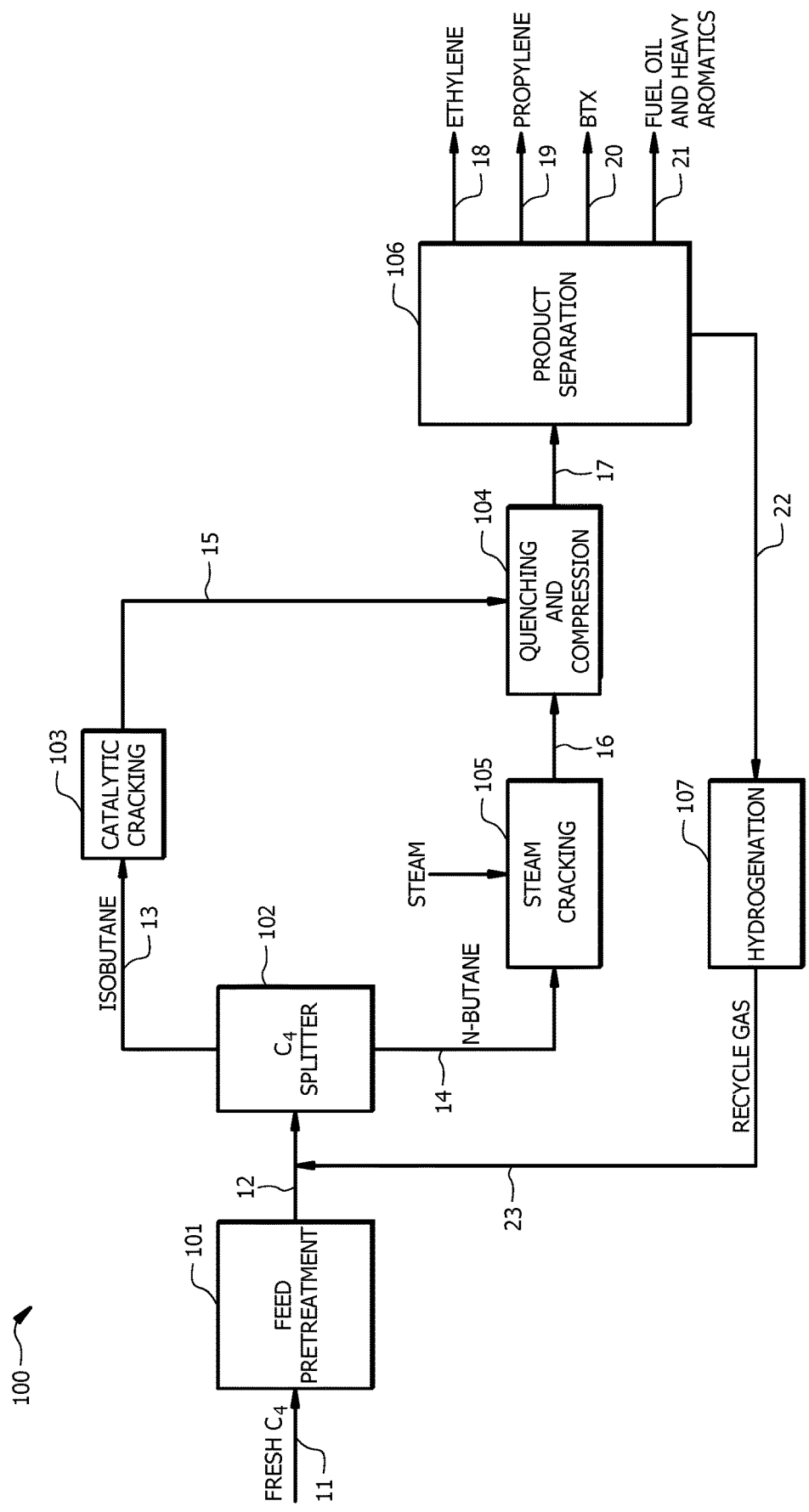
FIG. 1 shows a schematic diagram of a system for producing light olefins, according to embodiments of the invention.

In embodiments of the invention, the system for processing mixed $C_4$ paraffins and producing olefins and BTX can include an integrated system for splitting the mixed $C_4$ paraffins and processing the resulting fractions in different reaction units. With reference to FIG. 1, a schematic diagram is shown of system 100 that is capable of producing light olefins (e.g., $C_2$ and $C_3$ olefins) and BTX (benzene, toluene, xylene) with improved production efficiency and reduced production cost compared to conventional processes of steam cracking mixed $C_4$ paraffins. According to embodiments of the invention, system 100 may include feed pretreatment unit 101 configured to receive fresh $C_4$ stream 11 to remove impurities such as sulfur containing components and $CO_2$ to produce feed stream 12 comprising mixed $C_4$ paraffins. Fresh $C_4$ stream 11 may be obtained from refineries or any other source. In embodiments of the invention, feed pretreatment unit 101 may include sulfur and/or $CO_2$ guard beds, or combinations thereof. Fresh $C_4$ stream 11 may include n-butane, isobutene, and other components/impurities, or combinations thereof. Feed stream 12 may include 25 to 35 wt. % isobutane and 65 to 75 wt. % n-butane.

According to embodiments of the invention, an outlet of feed pretreatment unit 101 may be in fluid communication with $C_4$ splitter 102 such that feed stream 12 flows from feed pretreatment unit 101 to $C_4$ splitter 102. In embodiments of the invention, $C_4$ splitter 102 may be adapted to separate feed stream 12 into first stream 13 comprising primarily isobutane and second stream 14 comprising primarily n-butane. In embodiments of the invention, $C_4$ splitter 102 may include distillation columns, condensers, reboilers, or combinations thereof. First stream 13 may comprise 90 to 99.5 wt. % isobutane and all ranges and values there between including ranges of 90 to 90.5 wt. %, 90.5 to 91.0 wt. %, 91.0 to 91.5 wt. %, 91.5 to 92.0 wt. %, 92.0 to 92.5 wt. %, 92.5 to 93.0 wt. %, 93.0 to 93.5 wt. %, 93.5 to 94.0 wt. %, 94.0 to 94.5 wt. %, 94.5 to 95.0 wt. %, 95.0 to 95.5 wt. %, 95.5 to 96.0 wt. %, 96.0 to 96.5 wt. %, 96.5 to 97.0 wt. %, 97.0 to 97.5 wt. %, 97.5 to 98.0 wt. %, 98.0 to 98.5 wt. %, 98.5 to 99.0 wt. %, and 99.0 to 99.5 wt. %. Second stream 14 may comprise 85 to 99.5 wt. % n-butane and all ranges and values there between including 85 to 86 wt. %, 86 to 87 wt. %, 87 to 88 wt. %, 88 to 89 wt. %, 89 to 90 wt. %, 90 to 91 wt. %, 91 to 92 wt. %, 92 to 93 wt. %, 93 to 94 wt. %, 94 to 95 wt. %, 95 to 96 wt. %, 96 to 97 wt. %, 97 to 98 wt. %, 98 to 99 wt. %, and 99 to 99.5 wt. %.

In embodiments of the invention, a first outlet of $C_4$ splitter 102 may be in fluid communication with an inlet of catalytic cracking unit 103 such that first stream 13 flows from $C_4$ splitter 102 to catalytic cracking unit 103. According to embodiments of the invention, catalytic cracking unit 103 may be adapted to catalytically crack isobutane of first stream 13 to produce first effluent stream 15 comprising primarily propylene, ethylene, BTX, unreacted isobutane or combinations thereof. First effluent stream 15 may further comprise 1-butene, 2-butene, isobutylene, butadiene, methane, hydrogen, fuel oil, heavy aromatics, or combinations thereof. In embodiments of the invention, catalytic cracking unit 103 may comprise a reactor unit and a catalyst regenerator unit. The reactor unit of catalytic cracking unit 103 may include one or more fixed bed reactors, one or more fluidized bed reactors, one or more moving bed reactors, or combinations thereof. In embodiments of the invention, catalytic cracking unit 103 may include a catalyst comprising Fe modified HZSM-5, Cr modified HZSM-5, Ni modified HZSM-5, or combinations thereof. In embodiments of the invention, the catalyst regenerator unit may be adapted to regenerate spent catalyst from the reactor unit of catalytic cracking unit 103.

In embodiments of the invention, an outlet of catalytic cracking unit 103 may be in fluid communication with an inlet of quenching and compression unit 104 such that first effluent stream 15 flows from catalytic cracking unit 103 to quenching and compression unit 104. Quenching and compression unit 104 may be adapted to cool down and compress first effluent stream 15. According to embodiments of the invention, quenching and compression unit 104 may include columns, heat exchangers, separators/settlers and compressors, or combinations thereof.

In embodiments of the invention, a second outlet of $C_4$ splitter may be in fluid communication with steam cracking unit 105 such that second stream 14 flows from $C_4$ splitter to steam cracking unit 105. According to embodiments of the invention, steam cracking unit 105 may be adapted to steam crack hydrocarbons of second stream 14 to produce second effluent stream 16 comprising primarily propylene, ethylene, BTX, unreacted n-butane, or combinations thereof. Second effluent stream 16 may further comprise 1-butene, 2-butene, isobutylene, butadiene, methane, hydrogen, fuel oil, heavy aromatics, or combinations thereof. In embodiments of the invention, an outlet of steam cracking unit 105 may be in fluid communication with an inlet of quenching and compression unit 104 such that second effluent stream 16 flows from steam cracking unit 105 to quenching and compression unit 104. According to embodiments of the invention, quenching and compression unit 104 may be adapted to cool down and compress second effluent stream 16 and first effluent stream 15 to produce combined quenched stream 17. In embodiments of the invention, combined quenched stream 17 may include ethylene, propylene, BTX, fuel oil and heavy aromatics, 1-butene, 2-butene, isobutylene, butadiene, n-butane, isobutane, or combinations thereof.

According to embodiments of the invention, an outlet of quenching and compression unit 104 may be in fluid communication with product separation unit 106 such that combined quenched stream 17 flows from quenching compression unit 104 to product separation unit 106. In embodiments of the invention, product separation unit 106 may be adapted to separate combined quenched stream 17 into a plurality streams including ethylene stream 18 comprising primarily ethylene, propylene stream 19 comprising primarily propylene, BTX stream 20 comprising primarily BTX, heavy stream 21 comprising primarily fuel oil and heavy aromatics collectively, and recycle stream 22 comprising 1-butene, 2-butene, isobutylene, butadiene, n-butane, isobutane, or combinations thereof. According to embodiments of the invention, product separation unit 106 may include one or more distillation columns, absorbers, heat exchanger, or combinations thereof.

In embodiments of the invention, an outlet of product separation unit 106 may be in fluid communication with hydrogenation unit 107 such that recycle stream 22 flows from product separation unit 106 to hydrogenation unit 107. In embodiments of the invention, hydrogenation unit 107 may be adapted to hydrogenate at least some 1-butene, 2-butene, isobutylene, butadiene, or combinations thereof to produce hydrogenated recycle stream 23. Hydrogenated recycle stream 23 may include $C_4$ hydrocarbons, $C_5+$ hydrocarbons, or combinations thereof. In embodiments of the invention, hydrogenated recycle stream 23 may contain substantially no olefinic $C_4$ hydrocarbons. According to embodiments of the invention, hydrogenation unit may include one or more fixed bed reactor. In embodiments of the invention, hydrogenation unit 107 may comprise a hydrogenation catalyst including platinum, palladium, rhodium, nickel and ruthenium-based catalyst, or combinations thereof. In embodiments of the invention, an outlet of hydrogenation unit 107 may be in fluid communication with $C_4$ splitter 102 such that hydrogenated recycle stream 23 flows from hydrogenation unit 107 to $C_4$ splitter 102.

B. Method of Producing Olefins and BTX

Figure 2:
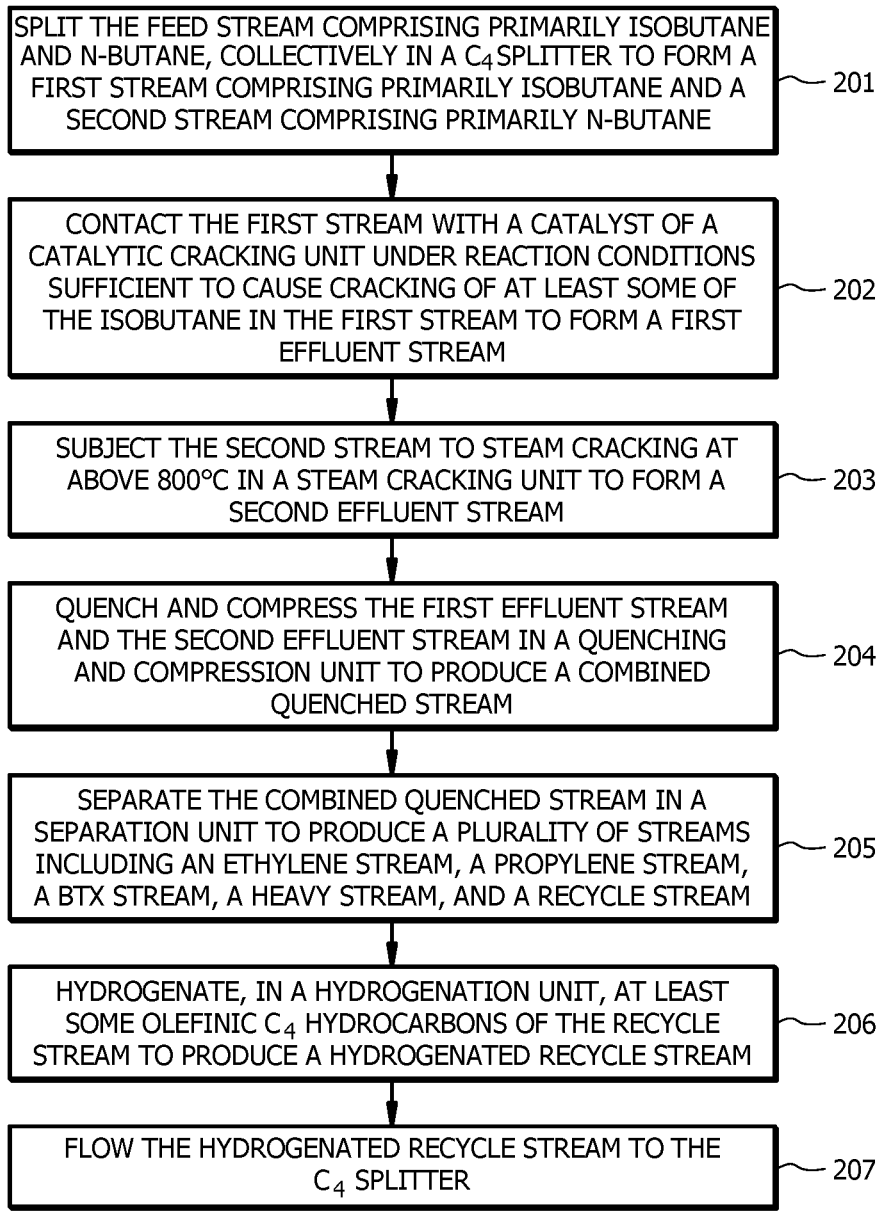
FIG. 2 shows a schematic flowchart of a method of producing light olefins, according to embodiments of the invention.

Methods of producing olefins and BTX using mixed $C_4$ paraffins have been discovered. The methods may be capable of improving the conversion rate of $C_4$ paraffins to light olefins and/or BTX and reducing the operation cost for producing light olefins and/or BTX compared to conventional methods that directly steam cracks mixed $C_4$ paraffins. As shown in FIG. 2, embodiments of the invention include method 200 for producing olefins. Method 200 may be implemented by system 100, as shown in FIG. 1. According to embodiments of the invention, as shown in block 201, method 200 may include splitting feed stream 12 comprising primarily isobutane and n-butane, collectively, to form first stream 13 comprising primarily isobutane and second stream 14 comprising primarily n-butane. In embodiments of the invention, feed stream 12 may comprise 25 to 25 wt. % isobutane and 65 to 75 wt. % n-butane.

In embodiments of the invention, $C_4$ splitter may include distillation columns, extractors, heat exchangers, or combinations thereof. Operating conditions of $C_4$ splitter may include an operating temperature of 20 to 150° C. and all ranges and values there between including ranges of 20 to 30° C., 30 to 40° C., 40 to 50° C., 50 to 60° C., 60 to 70° C., 70 to 80° C., 80 to 90° C., 90 to 100° C., 100 to 110° C., 110 to 120° C., 120 to 130° C., 130 to 140° C., and 140 to 150° C. Operating conditions of $C_4$ splitter may include an operating pressure of 5 to 10 bar and all ranges and values there between including 5 to 5.5 bar, 5.5 to 6.0 bar, 6.0 to 6.5 bar, 6.5 to 7.0 bar, 7.0 to 7.5 bar, 7.5 to 8.0 bar, 8.0 to 8.5 bar, 8.5 to 9.0 bar, 9.0 to 9.5 bar, and 9.5 to 10 bar. According to embodiments of the invention, first stream 13 may include 90 to 99.5 wt. % isobutane and all ranges and values there between including ranges of 90 to 91 wt. %, 91 to 92 wt. %, 92 to 93 wt. %, 93 to 94 wt. %, 94 to 95 wt. %, 95 to 96 wt. %, 96 to 97 wt. %, 97 to 98 wt. %, 98 to 99 wt. %, and 99 to 99.5 wt. %. Second stream 14 may include 85 to 99.5 wt. % n-butane and all ranges and values there between including ranges of 85 to 86 wt. %, 86 to 87 wt. %, 87 to 88 wt. %, 88 to 89 wt. %, 89 to 90 wt. %, 90 to 91 wt. %, 91 to 92 wt. %, 92 to 93 wt. %, 93 to 94 wt. %, 94 to 95 wt. %, 95 to 96 wt. %, 96 to 97 wt. %, 97 to 98 wt. %, 98 to 99 wt. %, and 99 to 99.5 wt. %.

According to embodiments of the invention, as shown in block 202, method 200 may further comprise contacting first stream 13 with a catalyst of catalytic cracking unit 103 under reaction conditions sufficient to cause cracking of at least some of the isobutane in first stream 13 to form first effluent stream 15. In embodiments of the invention, first effluent stream 15 may comprise 20 to 35 wt. % ethylene, 20 to 35 wt. % propylene, 10 to 25 wt. % BTX, 10 to 25 wt. % fuel gas, and 1 to 10 wt. % unreacted isobutane. In embodiments of the invention, first effluent stream 15 may further comprise 1-butene, 2-butene, isobutylene, butadiene, methane, hydrogen, fuel oil, heavy aromatics, or combinations thereof. In embodiments of the invention, the catalyst may be adapted to catalyze the cracking reaction of the hydrocarbons in first stream 15. The catalyst in catalytic cracking unit 103 may include Fe modified HZSM-5 catalyst, Cr modified HZSM-5, Ni modified HZSM-5, or combinations thereof. In embodiments of the invention, the reaction conditions at block 202 may include a reaction temperature of 575 to 625° C. and all ranges and values there between including ranges of 575 to 580° C., 580 to 585° C., 585 to 590° C., 590 to 595° C., 595 to 600° C., 600 to 605° C., 605 to 610° C., 610 to 615° C., 615 to 620° C., and 620 to 625° C. The reaction conditions at block 202 may further include a reaction pressure of 1 to 5 bar and all ranges and values there between including 1 to 1.5 bar, 1.5 to 2.0 bar, 2.0 to 2.5 bar, 2.5 to 3.0 bar, 3.0 to 3.5 bar, 3.5 to 4.0 bar, 4.0 to 4.5 bar, and 4.5 to 5.0 bar. The reaction conditions at block 202 may further include a weight hourly space velocity of 1000 to 6000 $hr^{-1}$ and all ranges and values there between including ranges of 1000 to 1500 $hr^{-1}$, 1500 to 2000 $hr^{-1}$, 2000 to 2500 $hr^{-1}$, 2500 to 3000 $hr^{-1}$, 3000 to 3500 $hr^{-1}$, 3500 to 4000 $hr^{-1}$, 4000 to 4500 $hr^{-1}$, 4500 to 5000 $hr^{-1}$, 5000 to 5500 $hr^{-1}$, and 5500 to 6000 $hr^{-1}$. In embodiments of the invention, the conversion rate of isobutane at block 202 may be in a range of 90 to 99% and all ranges and values there between including 90 to 91%, 91 to 92%, 92 to 93%, 93 to 94%, 94 to 95%, 95 to 96%, 96 to 97%, 97 to 98%, and 98 to 99%. According to embodiments of the invention, first effluent stream 15 may comprise 1 to 10 wt. % olefinic $C_4$ hydrocarbons including 1-butene, 2-butene, isobutylene, butadiene, or combinations thereof.

According to embodiments of the invention, as shown in block 203, method 200 may further include subjecting second stream 14 to steam cracking at a temperature above 800° C. in steam cracking unit 105 to form second effluent stream 16 comprising one or more of ethylene, propylene, benzene, toluene, and xylene. Second effluent stream 16 may further comprise 1-butene, 2-butene, isobutylene, butadiene, methane, hydrogen, fuel oil, heavy aromatics, unreacted n-butane, or combinations thereof. In embodiments of the invention, second effluent stream 16 may comprise 35 to 45 wt. % ethylene, 15 to 24 wt. % propylene, 1 to 7 wt. % BTX, and 2 to 10 wt. % unreacted butane. Second effluent stream 16 may comprise 10 to 20 wt. % olefinic $C_4$ hydrocarbons including 1-butene, 2-butene, isobutylene, butadiene, or combinations thereof.

In embodiments of the invention, a steam to hydrocarbon ratio fed to steam cracking unit 105 at block 203 may be in a range of 0.32 to 0.45 and all ranges and values there between including ranges of 0.32 to 0.33, 0.33 to 0.34, 0.34 to 0.35, 0.35 to 0.36, 0.36 to 0.37, 0.37 to 0.38, 0.38 to 0.39, 0.39 to 0.40, 0.40 to 0.41, 0.41 to 0.42, 0.42 to 0.43, 0.43 to 0.44, and 0.44 to 0.45. A residence time of steam cracking unit 105 for steam cracking at block 203 may be in a range of 3 to 10 ms and all ranges and values there between including 4 ms, 5 ms, 6 ms, 7 ms, 8 ms, and 9 ms. A conversion rate of n-butane at block 203 may be in a range of 85 to 95% and all ranges and values there between including ranges of 85 to 86%, 86 to 87%, 87 to 88%, 88 to 89%, 89 to 90%, 90 to 91%, 91 to 92%, 92 to 93%, 93 to 94%, and 94 to 95%.

According to embodiments of the invention, as shown in block 204, method 200 may further comprise quenching and compressing first effluent stream 15 and second effluent stream 16 in quenching and compression unit 104 to produce combined quenched stream 17. In embodiments of the invention, the quenching and compressing at block 204 may include quenching first effluent stream 15 and second effluent stream 16 (and the subsequent combined quenched stream 17) to a temperature of 83 to 93° C. and all range and values there between including 84° C., 85° C., 86° C., 87° C., 88° C., 89° C., 90° C., 91° C., and 92° C. The quenching and compressing at block 204 may further include compressing the first effluent stream 15 and second effluent stream 16 (and the subsequent combined quenched stream 17) to a pressure in a range of 10 to 35 bar and all ranges and values there between including 10 to 12 bar, 12 to 14 bar, 14 to 16 bar, 16 to 18 bar, 18 to 20 bar, 20 to 22 bar, 22 to 24 bar, 24 to 26 bar, 26 to 28 bar, 28 to 30 bar, 30 to 32 bar, 32 to 34 bar, and 34 to 35 bar.

According to embodiments of the invention, as shown in block 205, method 200 may further comprise separating the combined quenched stream 17 in product separation unit 106 to produce a plurality of streams including ethylene stream 18 comprising primarily ethylene, propylene stream 19 comprising primarily propylene, BTX stream 20 comprising primarily BTX, heavy stream 21 comprising primarily fuel oil and heavy aromatics, collectively. In embodiments of the invention, the separating at block 205 may further produce recycle stream 22 comprising 1-butene, 2-butene, butadiene, isobutylene, n-butane, isobutane, or combinations thereof. In embodiments of the invention, ethylene stream 18 may comprise 99 to 99.95 wt. % ethylene. Propylene stream 19 may comprise 99 to 99.95 wt. % propylene. BTX stream 20 may comprise 45 to 60 wt. % benzene, 35 to 45 wt. % toluene, and 20 to 40 wt. % xylene. Recycle stream 22 may comprise 40 to 75 wt. % olefinic $C_4$ hydrocarbons. In embodiments of the invention, the flowrate ratio between recycle stream 22 and feed stream 12 may be in a range of 18 to 28 and all ranges and values there between including 19, 20, 21, 22, 23, 24, 25, 26, and 27.

According to embodiments of the invention, as shown in block 206, method 200 may further comprise hydrogenating, in hydrogenation unit 107, at least some olefinic $C_4$ hydrocarbons of recycle stream 22 comprising 1-butene, 2-butene, isobutylene, butadiene, or combinations thereof to produce hydrogenated recycle stream 23. In embodiments of the invention, hydrogenated recycle stream 23 may comprise 1 to 3 wt. % olefinic $C_4$ hydrocarbons. In embodiments of the invention, hydrogenating at block 206 may be carried out at a hydrogenation temperature of 100 to 260° C. and all ranges and values there between including ranges of 100 to 110° C., 110 to 120° C., 120 to 130° C., 130 to 140° C., 140 to 150° C., 150 to 160° C., 160 to 170° C., 170 to 180° C., 180 to 190° C., 190 to 200° C., 200 to 210° C., 210 to 220° C., 220 to 230° C., 230 to 240° C., 240 to 250° C., and 250 to 260° C. Hydrogenating at block 206 may be carried out at a hydrogenation pressure of 10 to 70 bar and all ranges and values there between including 10 to 15 bar, 15 to 20 bar, 20 to 25 bar, 25 to 30 bar, 30 to 35 bar, 35 to 40 bar, 40 to 45 bar, 45 to 50 bar, 50 to 55 bar, 55 to 60 bar, 60 to 65 bar, and 65 to 70 bar. According to embodiments of the invention, the flowrate ratio between hydrogen and recycle stream 22 feeding to hydrogenation unit 107 may be in a range of 0.01 to 0.04 and all ranges and values there between including 0.01 to 0.015, 0.015 to 0.020, 0.020 to 0.025, 0.025 to 0.030, 0.030 to 0.035, and 0.035 to 0.040. A liquid hourly space velocity for hydrogenation unit 107 at block 206 may be in a range of 0.1 to 40 $hr^{-1}$ and all ranges and values there between including ranges of 0.1 to 0.2 $hr^{-1}$, 0.2 to 0.3 $hr^{-1}$, 0.3 to 0.4 $hr^{-1}$, 0.4 to 0.5 $hr^{-1}$, 0.5 to 0.6 $hr^{-1}$, 0.6 to 0.7 $hr^{-1}$, 0.7 to 0.8 $hr^{-1}$, 0.8 to 0.9 $hr^{-1}$, 0.9 to 1.0 $hr^{-1}$, 1.0 to 2.0 $hr^{-1}$, 2.0 to 3.0 $hr^{-1}$, 3.0 to 4.0 $hr^{-1}$, 4.0 to 5.0 $hr^{-1}$, 5.0 to 6.0 $hr^{-1}$, 6.0 to 7.0 $hr^{-1}$, 7.0 to 8.0 $hr^{-1}$, 8.0 to 9.0 $hr^{-1}$, 9.0 to 10 $hr^{-1}$, 10 to 15 $hr^{-1}$, 15 to 20 $hr^{-1}$, 20 to 25 $hr^{-1}$, 25 to 30 $hr^{-1}$, 30 to 35 $hr^{-1}$, and 35 to 40 $hr^{-1}$. In embodiments of the invention, method 200 may further comprise flowing hydrogenated recycle stream 23 to $C_4$ splitter 102, as shown in block 207. Alternatively or additionally, according to embodiments of the invention, hydrogenated recycle stream 23 may be flowed into feed stream 12 before being flowed into $C_4$ splitter 102.

Although embodiments of the present invention have been described with reference to blocks of FIG. 2, it should be appreciated that operation of the present invention is not limited to the particular blocks and/or the particular order of the blocks illustrated in FIG. 2. Accordingly, embodiments of the invention may provide functionality as described herein using various blocks in a sequence different than that of FIG. 2.

As part of the disclosure of the present invention, a specific example is included below. The example is for illustrative purposes only and is not intended to limit the invention. Those of ordinary skill in the art will readily recognize parameters that can be changed or modified to yield essentially the same results.

EXAMPLE

Simulations on the processes of producing light olefins and BTX according to embodiments of the invention and the conventional method of steam cracking mixed $C_4$ hydrocarbons were run on a Pro II platform. The results were compared. In the simulations on both the process of the present invention and the conventional method, the feed stream contained 30 wt. % isobutane and 70 wt. % n-butane. For the process of the present invention, the isobutane and the n-butane were separated. The resulting isobutane was catalytically cracked and the resulting n-butane was processed in a steam cracking unit. For the process of the conventional method, mixed $C_4$ hydrocarbons were directly processed in a steam cracking unit. The results of the simulations showed that the method according to the invention produced 12% more ethylene, 7% less propylene, and 104% more BTX than the conventional method. Furthermore, the method according to embodiments of the invention was capable of significantly reducing the production of fuel oil and heavy aromatics. Moreover, the method according to embodiments of the invention reduced the flowrate of the recycle stream containing olefinic $C_4$ hydrocarbons by about 25%. Consequently, the hydrogen and energy used during hydrogenation of the recycle stream were reduced.

In the context of the present invention, at least the following 15 embodiments are described. Embodiment 1 is a method of producing olefins. The method includes splitting a feed stream containing primarily isobutane and n-butane, collectively, to form a first stream containing primarily isobutane and a second stream containing primarily n-butane. The method also includes contacting the first stream with a catalyst under reaction conditions sufficient to cause cracking of at least some of the isobutane in the first stream to form one or more of: ethylene, propylene, benzene, toluene, and xylene. The method further includes subjecting the second stream to steam cracking at a temperature above 800° C. to form one or more of: ethylene, propylene, benzene, toluene, and xylene. Embodiment 2 is the method of embodiment 1, wherein the catalyst contains Fe modified HZSM-5. Embodiment 3 is the method of either of embodiments 1 or 2, wherein the reaction conditions in the contacting step include a reaction temperature in a range of 575 to 625° C. Embodiment 4 is the method of any of embodiments 1 to 3, wherein the reaction conditions in the contacting step include a reaction pressure of 1 to 5 bar. Embodiment 5 is the method of any of embodiments 1 to 4, wherein the feed stream includes 25 to 35 wt. % isobutane and 65 to 75 wt. % n-butane. Embodiment 6 is the method of any of embodiments 1 to 5, wherein the contacting step is carried out in a catalytic cracking unit. Embodiment 7 is the method of embodiment 6, further including flowing an effluent from the catalytic cracking unit to a quenching and compression unit. Embodiment 8 is the method of any of embodiments 1 to 7, wherein the subjecting step is carried out in a steam cracking unit. Embodiment 9 is the method of embodiment 8, further including flowing an effluent from the steam cracking unit to a quenching and compression unit. Embodiment 10 is the method of embodiment 9, wherein the effluent from the catalytic cracking unit and the effluent from the steam cracking unit are flowed to the same quenching and compression unit to produce a combined quenched stream. Embodiment 11 is the method of embodiment 10, further including separating the combined quenched stream in a separation unit to produce a plurality streams including an ethylene stream containing primarily ethylene, a propylene stream containing primarily propylene, a BTX stream containing primarily BTX, and a heavy stream containing primarily fuel oil and $C_9+$ aromatics. Embodiment 12 is the method of embodiment 11, wherein the separating further produces a recycle stream containing 1-butene, 2-butene, butadiene, isobutylene, n-butane, isobutane, or combinations thereof. Embodiment 13 is the method of embodiment 12, wherein a flowrate ratio of the recycle stream to the feed stream is 0.15 to 0.30. Embodiment 14 is the method of either of embodiments 12 or 13, further including hydrogenating at least some 1-butene, 2-butene, isobutylene and/or butadiene of the recycle stream in a hydrogenation unit to produce a hydrogenated recycle stream and flowing the hydrogenated recycle stream to the feed stream. Embodiment 15 is the method of any of embodiments 1 to 14, wherein the isobutane and the n-butane are converted to ethylene, propylene, and BTX at a combined conversion rate of 70 to 85%.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of producing olefins, the method comprising:
   splitting a feed stream comprising primarily isobutane and n-butane, collectively, to form a first stream comprising primarily isobutane and a second stream comprising primarily n-butane;
   contacting the first stream with a catalyst under reaction conditions sufficient to cause cracking of at least some of the isobutane in the first stream to form one or more of:
   ethylene, propylene, benzene, toluene, and xylene; and
   subjecting the second stream to steam cracking at a temperature above 800° C. to form one or more of benzene, toluene, and xylene.

2. The method of claim 1, wherein the catalyst comprises Fe modified HZSM-5.

3. A method of producing olefins, the method comprising:
   splitting a feed stream comprising primarily isobutane and n-butane, collectively, to form a first stream comprising primarily isobutane and a second stream comprising primarily n-butane;
   contacting the first stream with a catalyst under reaction conditions sufficient to cause cracking of at least some of the isobutane in the first stream to form one or more of:
   ethylene, propylene, benzene, toluene, and xylene; and
   subjecting the second stream to steam cracking at a temperature above 800° C. to form one or more of ethylene, propylene, benzene, toluene, and xylene,
   wherein the reaction conditions in the contacting step comprise a reaction temperature in a range of 575 to 625° C.

4. The method of claim 1, wherein the reaction conditions in the contacting step comprise a reaction pressure of 2 to 5 bar.

5. The method of claim 1, wherein the feed stream comprises 25 to 35 wt. % isobutane and 65 to 75 wt. % n-butane.

6. The method of claim 3, wherein the catalyst comprises Fe modified HZSM-5.

7. The method of claim 6, further comprising flowing an effluent from the catalytic cracking unit to a quenching and compression unit.

8. The method of claim 1, wherein the subjecting step is carried out in a steam cracking unit.

9. The method of claim 8, further comprising flowing an effluent from the steam cracking unit to a quenching and compression unit.

10. The method of claim 9, wherein the effluent from the catalytic cracking unit and the effluent from the steam cracking unit are flowed to the same quenching and compression unit to produce a combined quenched stream.

11. The method of claim 10, further comprising separating the combined quenched stream in a separation unit to produce a plurality streams including an ethylene stream comprising primarily ethylene, a propylene stream comprising primarily propylene, a BTX stream comprising primarily BTX, and a heavy stream comprising primarily fuel oil and $C_9+$ aromatics.

12. The method of claim 11, wherein the separating further produces a recycle stream comprising 1-butene, 2-butene, butadiene, isobutylene, n-butane, isobutane, or combinations thereof.

13. The method of claim 12, wherein a flowrate ratio of the recycle stream to the feed stream is 0.15 to 0.30.

14. The method of claim 12, further comprising:
   hydrogenating at least some 1-butene, 2-butene, isobutylene and/or butadiene of the recycle stream in a hydrogenation unit to produce a hydrogenated recycle stream; and
   flowing the hydrogenated recycle stream to the feed stream.

15. The method of claim 3, wherein one or more of the benzene, the toluene, and the xylene are formed.

16. The method of claim 2, wherein the isobutane and the n-butane are converted to each of ethylene, propylene, and BTX at a combined conversion rate of 70 to 85%.

17. The method of claim 3, wherein the isobutane and the n-butane are converted to ethylene, propylene, and BTX at a combined conversion rate of 70 to 85%.

18. The method of claim 4, wherein the isobutane and the n-butane are converted to ethylene, propylene, and BTX at a combined conversion rate of 70 to 85%.

19. The method of claim 5, wherein the isobutane and the n-butane are converted to ethylene, propylene, and BTX at a combined conversion rate of 70 to 85%.

20. The method of claim 6, wherein the isobutane and the n-butane are converted to ethylene, propylene, and BTX at a combined conversion rate of 70 to 85%.

* * * * *